US 6,678,962 B1

(12) United States Patent
Love et al.

(10) Patent No.: US 6,678,962 B1
(45) Date of Patent: Jan. 20, 2004

(54) DEVICE AND METHOD FOR ASSESSING THE GEOMETRY OF A HEART VALVE

(75) Inventors: Jack W. Love, Santa Barbara, CA (US); James G. Hanlon, Camarillo, CA (US)

(73) Assignee: Cardiomend LLC, Santa Barbara, CA (US)

( * ) Notice: Subject to any disclaimer, the term of this patent is extended or adjusted under 35 U.S.C. 154(b) by 0 days.

(21) Appl. No.: 09/716,140

(22) Filed: Nov. 17, 2000

Related U.S. Application Data

(60) Provisional application No. 60/165,977, filed on Nov. 17, 1999.

(51) Int. Cl.[7] ............................................... A61B 5/103
(52) U.S. Cl. .......................... 33/512; 33/555.1; 33/542
(58) Field of Search ........................ 33/511, 512, 555.1, 33/501.45, 542, 543; 623/2.11; 600/587

(56) References Cited

U.S. PATENT DOCUMENTS

| | | | |
|---|---|---|---|
| 2,706,338 A | * 4/1955 | Ackerman | 33/509 |
| 3,161,041 A | * 12/1964 | Amburgey | 33/509 |
| 3,875,668 A | * 4/1975 | Taylor | 33/509 |
| 4,211,241 A | * 7/1980 | Kaster et al. | 33/512 |
| 4,470,157 A | * 9/1984 | Love | 623/2.15 |
| 5,042,161 A | * 8/1991 | Hodge | 33/501.45 |
| 5,360,014 A | 11/1994 | Sauter et al. | |
| 5,489,296 A | 2/1996 | Love et al. | |
| 5,571,174 A | * 11/1996 | Love et al. | 29/890.12 |
| 5,603,165 A | * 2/1997 | Bernhardt et al. | 33/509 |
| 5,697,382 A | * 12/1997 | Love et al. | 623/901 |
| 5,716,399 A | 2/1998 | Love | |
| 5,814,096 A | * 9/1998 | Lam et al. | 623/2.11 |
| 5,961,539 A | 10/1999 | Northrup, III et al. | |
| 6,019,739 A | 2/2000 | Rhee et al. | |
| 6,042,554 A | * 3/2000 | Rosenman et al. | 623/2.11 |
| 6,129,758 A | 10/2000 | Love | |
| 6,319,281 B1 | * 11/2001 | Patel | 623/2.3 |
| 6,350,281 B1 | * 2/2002 | Rhee | 33/512 |
| 6,383,147 B1 | * 5/2002 | Stobie | 600/587 |
| 6,425,902 B1 | * 7/2002 | Love | 623/2.11 |
| 6,575,921 B2 | * 6/2003 | Vanden Hoek et al. | 600/587 |
| 6,578,281 B2 | * 6/2003 | Takahashi | 33/555.1 |
| 6,598,307 B2 | * 7/2003 | Love et al. | 33/512 |
| 2002/0133226 A1 | * 9/2002 | Marquez et al. | 623/2.11 |
| 2003/0078651 A1 | * 4/2003 | Schoon et al. | 623/2.11 |

OTHER PUBLICATIONS

Swanson, W. Milton; Clark, Richard E., Dimentions and Geometric Relationships of the Human Aortic Value as a Function of Pressure, Circulation Research, vol. 55, Dec. 1974.

Zioupos, P.; Barbanel, J. C.; Fisher, J., Mechanical and optical anisotropy of bovine pericardium, Medical & Biological Computing, Jan. 1992.

Zioupos, P.; Barbanel, J. C.; Fisher, J.; Wheatly, D.J., Changes in the mechanical properties of bioprosthetic valve leaflets made of bovine pericardium, as a result of long-term conditioning in vitro and implantation in vivo, Journal of Materials and Medicine 4 (1993) 531–537.

(List continued on next page.)

Primary Examiner—Christopher W. Fulton
Assistant Examiner—Yaritza Guadalupe
(74) Attorney, Agent, or Firm—Bryan Cave LLP

(57) ABSTRACT

A sizer for assessing the geometry of a heart valve annulus. The sizer preferably includes a circular sizing portion for measuring the diameter of the valve annulus. The sizing portion has radial spokes. The spokes are used to compare the symmetry of the commissures to the expected symmetry of a normal heart valve. The sizer preferably has one or more legs attached to the sizing portion for comparing the contour of the line of valve leaflet attachment to the expected contour of a normal heart valve having a diameter substantially equivalent to the measured diameter of the valve annulus.

11 Claims, 2 Drawing Sheets

OTHER PUBLICATIONS

Ioupos, P.; Barbanel, J. C.; Fisher, J., Anisotropic elasticity and strength of glutaraldehyde fixed bovine pericardium for use in pericardial bioprosthetic valves, Journal of Biomedical Materials Researchm Vo. 28, 49–57 (1994).

Zioupos, P.; Barbanel, J. C., Mechanics of native bovine pericardium, Biomaterials 1994, vol. 15, No. 9.

Hanlon, James C.; Suggit, Robert W.; Gibbs, Evan; McMeeking, Robert M.; Love, Jack W., Geometric Optimization of a Tissue Pattern for Semilunar Valve Reconstruction, J. Heart Valve Dis, vol. 8, No. 6, Nov. 1999.

Love, Jack W., Autologous Pericardial Reconstruction of Semilunar Valves, J Heart Valve Dis, /vol. 7, No. 1, Jan. 1998.

* cited by examiner

DEVICE AND METHOD FOR ASSESSING THE GEOMETRY OF A HEART VALVE

CROSS-REFERENCE TO RELATED APPLICATION

This application claims the benefit of U.S. Provisional Application No. 60/165,977, filed Nov. 17, 1999.

FIELD OF THE INVENTION

This invention relates to measuring instruments and methods and is particularly directed to instruments and methods used to measure the size and dimensions of heart valves in the surgical operating room at the time of heart valve reconstruction or replacement.

BACKGROUND OF THE INVENTION

When a surgeon must replace one or more of a patient's heart valves because of disease or defect of the native valve(s), the surgeon must identify the diameter of the patient's annulus in order to select the correct size replacement heart valve. The measurement of heart valve diameter in the operating room is typically done with some type of plug gauge. Gradated sizes of plug gauges, typically in 2 millimeter increments are used to find the best fit for any given valve annulus. The advent of homograft valves and, more recently, methods for reconstructing heart valves, makes it desirable to determine more than simply the best fit diameter. For operations involving the use of homograft valves, stentless heterograft valves, and any one of several methods of aortic or pulmonic heart valve reconstruction being used, it is also desirable to measure the height of the leaflets and the symmetry, or lack thereof, of the valve commissures. To meet these requirements, an instrument and methods have been developed that can be used in the operating room to assess valve geometry more completely than has been possible in the past.

SUMMARY OF THE INVENTION

The present invention is comprised of methods and instruments that can be used to measure the diameter of the valve annulus at the commissural level, to compare the height and lines of attachment of the individual leaflets with reference to a normalized geometry, and to determine the symmetry of the valve commissures. One preferred embodiment of the present invention comprises a circular piece with three equally spaced radial spokes that converge in the center to a socket to which a handle can be attached. Curved legs that correspond to the geometry of the normal native valve leaflet anatomy, as described in published medical articles, are attached to the circular piece.

In a typical operation to replace or to reconstruct an aortic or pulmonic valve, the diseased native valve is removed down to the annulus of the valve. After this has been done, the valve is sized. With the present invention, sizers of graded dimensions are used until the best-fit diameter at the commissural level is determined. With that sizer inserted in the aortic or pulmonic root, the height of each leaflet from its base to the apex of its commissures can be compared with the expected dimensions for that valve, based on published dimensions. The symmetry of the valve can be judged by aligning any given radial spokes of the circular piece with one commissure, and then noting the spacing of the remaining two commissures. The radial spokes each have a width that corresponds to an arc of the circle that encompasses the normal expected variation from perfect symmetry. Deviations from expected normal leaflet height or symmetry can be readily appreciated and used to increase the precision of the planned surgical procedure.

The drawings are provided for illustrative purposes only and should not be used to unduly limit the scope of the invention.

DETAILED DESCRIPTION OF THE INVENTION

Figure 1:
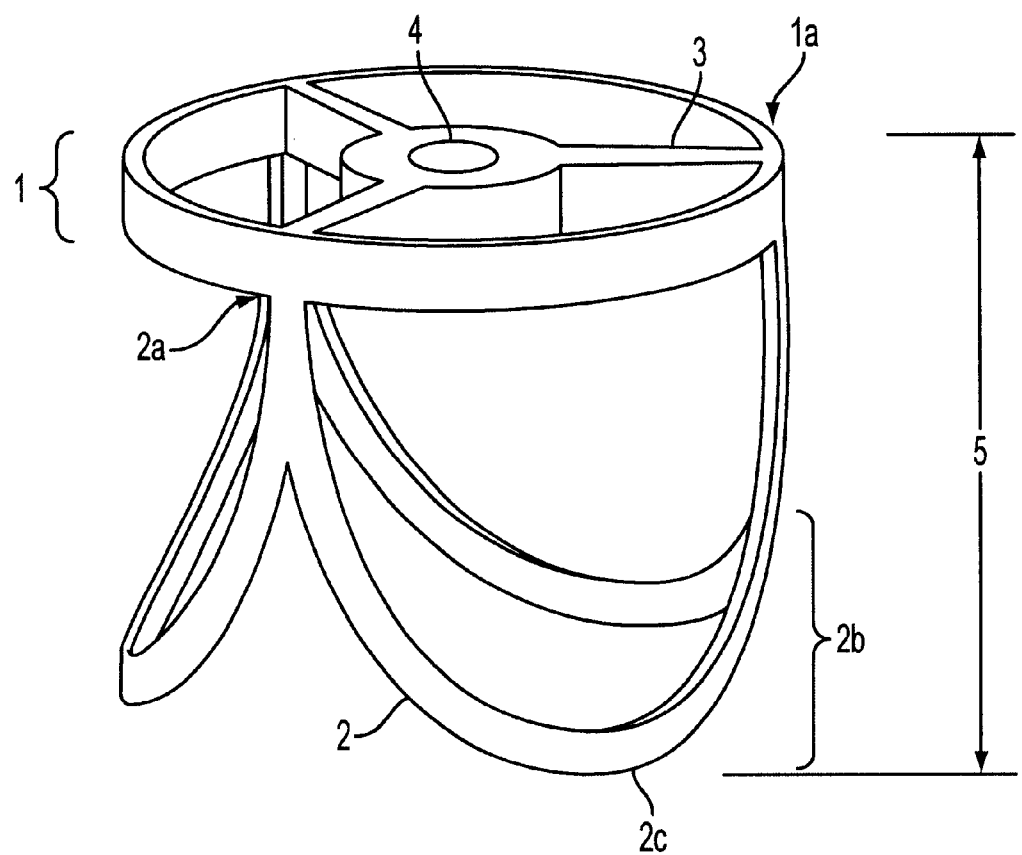
FIG. 1 is an oblique view from the side of the sizer of one preferred embodiment of the present invention.
Figure 2:
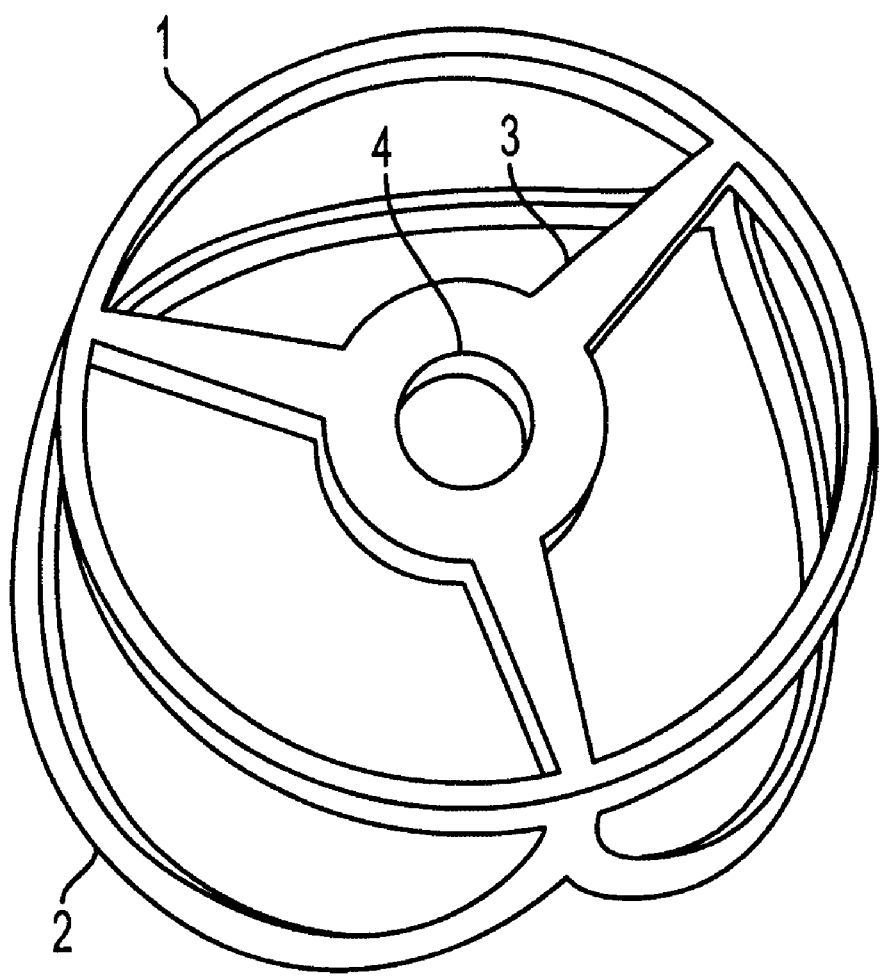
FIG. 2 is an oblique view from the top of the sizer of FIG. 1.

FIG. 1 and FIG. 2 represent two views of a sizer for assessing the geometry of a heart valve annulus by measuring annulus size, leaflet height, and leaflet symmetry of semilunar heart valves and is one preferred embodiment of the present invention. Obviously, modifications of the present invention can be made to measure annulus size and leaflet dimensions of tricuspid and mitral valves. The instrument is preferably molded, cast or machined as a single unit, preferably from a biocompatible thermoplastic material that can be readily sterilized and discarded after single use. The material preferably has sufficient rigidity to maintain its shape during the sizing procedure, but also a degree of malleability to make it easy to insert into and withdraw from the valve root without damaging the tissue. All edges that contact tissue are round and smooth to avoid damage to the tissue.

In FIG. 1, the sizing portion 1 is used to measure the diameter of the valve orifice at the commissural level. The sizing portion 1 is preferably circular. One or more legs 2 define the contoured line of attachment of a normal leaflet. Each leg preferably has an arched shape substantially conforming to the expected contour of a normal heart valve having a diameter substantially equivalent to the diameter of the sizing portion. As used herein the term "normal heart valve" generally refers to a heart valve having standard geometry and dimensions. However, the term "normal heart valve" is intended to broadly encompass any heart valve dimensions used as a standard of comparison. As used herein the term "diameter substantially equivalent to the measured diameter" is used broadly to refer to a diameter that is the same as, corresponding to, within a range of, or at a set variance from the measured diameter. Each leg has a proximal end 2a attached to the sizing portion 1 and a distal end 2b. The distal end 2b preferably has an arced shape with an apex 2c. Leaflet height is the dimension 5 which represents the distance from the top of the circular piece 1 to the apex 2c of leg 2. This corresponds to the predetermined heart valve leaflet height which is a ratio of the diameter of the circular piece 1.

Symmetry is assessed by aligning one of a plurality of radial spokes 3 of the sizing portion with a commissure of the native valve, and then comparing the alignment of the remaining two commissures with the other two radial spokes of the circular piece. Each spoke 3 is preferably connected to the perimeter 1a of the circular sizing portion 1 such that the width of each spoke at the perimeter 1a corresponds to an arc width on the perimeter 1a that corresponds to an acceptable small normal variation from perfect symmetry. The three spokes 3 are united in the center of the circular piece 1 by a socket 4 to which a handle can be removeably attached, either by a threaded connection or by some other quick connect-disconnect device.

In FIG. 2, some of these same components are identified. The circular portion 1 has the curved legs 2 to mark the leaflet line of attachment to the annulus. The radial spokes 3 are joined to the central socket 4.

The sizer with handle attached is placed in the aortic or pulmonic root so that the circular sizing portion is at the level of the commissures. Individual leaflet height and the line of leaflet attachment to the annulus are determined by comparing the curved legs 2 with the native valve geometry. Commissural symmetry is assessed by aligning one spoke with any one commissure and then noting the relationship of the other spokes with the other commissures. If all three commissures align within the width of the spokes where they intersect with the perimeter 1a of the circular portion 1, the native valve is symmetrical within normal the normal range of variation.

The sizer can be used in any semilunar heart valve operation where it is desirable to know the root diameter, leaflet height and line of attachment, and commissural symmetry. Such operations include, but are not limited to, valve reconstruction with tissue, autologous, homologous or heterologous, valve replacement with a homograft or any type of stentless heterograft, and pulmonary valve autotransplantation to the aortic position.

Changes, modification, variations and other uses of the subject invention will be and become apparent to those skilled in the art after considering this specification and the accompanying drawings which disclose the preferred embodiments thereof. All such changes, modification and variations and other uses and applications which do not depart from the spirit and scope of the invention are deemed to be covered by the invention. Therefore, it should be clearly understood that the forms of the present invention described above and shown in the Figures of the accompanying drawings are illustrative only and are not intended to limit the scope of the present invention.

We claim:

1. A sizer for a heart valve annulus having a diameter and a contoured line of valve leaflet attachment defining a leaflet shape, the sizer comprising:
   a first substantially circular diameter sizing portion for measuring the diameter of the valve annulus; and
   a second leaflet sizing portion comprising one or more arched members attached to the diameter sizing portion for assessing the leaflet shape, the leaflet sizing portion comprising one or more arched members, each of which substantially conforms to a predetermined heart valve leaflet height.

2. The sizer of claim 1, wherein each of the arched members substantially conforms to the expected shape of a leaflet of a normal heart valve.

3. The sizer of claim 1, wherein each of the arched members has a proximal end attached to the diameter sizing portion and an arced distal end having an apex, wherein the length of said arched member from the proximal end to the apex of the distal end corresponds to said predetermined leaflet height.

4. The sizer of claim 3, wherein the predetermined leaflet height approximates the expected height of a leaflet of a normal heart valve having a diameter substantially equivalent to the diameter of the diameter sizing portion.

5. The sizer of claim 1, wherein the one or more arched members is three arched members.

6. The sizer of claim 1, wherein the diameter sizing portion further comprises a socket for attaching a handle to the sizer.

7. A sizer for a heart valve annulus having a diameter, a contoured line of valve leaflet attachment defining a leaflet height, and a plurality of commissures, the sizer comprising:
   a first circular diameter sizing portion for measuring the diameter of the valve annulus; and
   a second leaflet sizing portion comprising one or more arched members attached to the diameter sizing portion for measuring the leaflet height wherein each arched member has a proximal end attached to the diameter sizing portion and an arced distal end having an apex, and the length of each arched member from the proximal end to the apex of the distal end is substantially equal to a predetermined leaflet height.

8. The sizer of claim 7, wherein each of the one or more arched members substantially conforms to the expected shape of a leaflet of a normal heart valve.

9. The sizer of claim 7, wherein the predetermined leaflet height approximates the expected height of a leaflet of a normal heart valve having a diameter substantially equivalent to the diameter of the diameter sizing portion.

10. The sizer of claim 7, wherein the diameter sizing portion has a perimeter, the diameter sizing portion further comprising three radial spokes connected to the perimeter of the circular sizing portion such that the width of each spoke at the perimeter designates an arc width that corresponds to a predetermined acceptable variation from normal symmetry.

11. A sizer for a heart valve annulus having a contoured line of valve leaflet attachment defining a shape of three valve leaflets, three commissures, and a diameter, the sizer comprising:
   a first circular diameter sizing portion for measuring the diameter of the valve annulus, the diameter sizing portion comprising a plurality of radial spokes for comparing the symmetry of the commissures to the expected symmetry of a normal heart valve; and
   a second leaflet sizing portion comprising three arched members attached to the diameter sizing portion for assessing the leaflet shape, each arched member comprising:
      a proximal end attached to the diameter sizing portion; and
      an arced distal end having an apex, wherein the length of the arched member from the proximal end to the apex of the distal end approximates the expected leaflet height of a normal heart valve having a diameter substantially equivalent to the diameter of the diameter sizing portion.

* * * * *